(12) United States Patent
Wake et al.

(10) Patent No.: US 7,446,875 B2
(45) Date of Patent: Nov. 4, 2008

(54) APPARATUS AND METHOD FOR ACQUIRING TIME-RESOLVED MEASUREMENTS UTILIZING DIRECT DIGITIZATION OF THE TEMPORAL POINT SPREAD FUNCTION OF THE DETECTED LIGHT

(75) Inventors: Robert H. Wake, Cooper City, FL (US); Steven L. Ponder, Ft. Lauderdale, FL (US)

(73) Assignee: Imaging Diagnostic Systems, Inc., Plantation, FL (US)

( * ) Notice: Subject to any disclaimer, the term of this patent is extended or adjusted under 35 U.S.C. 154(b) by 301 days.

(21) Appl. No.: 11/270,812

(22) Filed: Nov. 10, 2005

(65) Prior Publication Data

US 2006/0149150 A1    Jul. 6, 2006

Related U.S. Application Data

(60) Provisional application No. 60/627,147, filed on Nov. 15, 2004.

(51) Int. Cl.
*G01N 21/00* (2006.01)
(52) U.S. Cl. ...................................... 356/432
(58) Field of Classification Search ........................ None
See application file for complete search history.

(56) References Cited

U.S. PATENT DOCUMENTS

| | | | |
|---|---|---|---|
| 4,972,423 A | 11/1990 | Alfano et al. | |
| 5,119,815 A | 6/1992 | Chance | |
| 5,148,031 A | 9/1992 | Kamalov et al. | |
| 5,371,368 A | 12/1994 | Alfano et al. | |
| 5,386,827 A | 2/1995 | Chance et al. | |
| 5,555,885 A | 9/1996 | Chance | |
| 5,752,519 A | 5/1998 | Benaron et al. | |
| 6,339,216 B1 | 1/2002 | Wake | |
| 2004/0181153 A1* | 9/2004 | Hall | 600/448 |

OTHER PUBLICATIONS

Patterson et al., "Time resolved reflectance ad transmittance for the non-invasive measurement of tissue optical properties", Applied Optics, Jun. 15, 1989, vol. 28 No. 12, pp. 2331-2336.

(Continued)

*Primary Examiner*—Michael P Stafira
(74) *Attorney, Agent, or Firm*—Shlesinger, Arkwright & Garvey LLP

(57) ABSTRACT

An apparatus for acquiring time-resolved measurements from a sample from optical scanning comprises pulsed laser light directed to the sample; a first detector disposed to detect the light after exiting from the sample, the detected light being in the form of a first temporal point spread function (TPSF); a first amplifier to amplify the first TPSF; a first analog-to-digital converted (ADC) to directly digitize the first TPSF; a first buffer connected to the first ADC; a time-pickoff detector to initiate the first ADC to digitize the first TPSF; a clock burst generator initiated by the time-pickoff detector to provide conversion timing to the first ADC; and a computer programmed to fit the digitized first TPSF to a theoretical curve to extract its amplitude, and attenuation and scattering coefficients.

A method for acquiring time-resolved measurements from a sample from optical scanning comprises directing a pulse of light onto a surface of the sample; detecting the light that exits from the sample in the form of a temporal point spread function (TPSF); directly digitizing the TPSF; and extracting a transport scattering coefficient and a absorption coefficient from the digitized TPSF.

17 Claims, 6 Drawing Sheets

OTHER PUBLICATIONS

J. Swartling et al., "Diffuse time-resolved reflectance and transmittance measurements of the female breast using different interfiber distances in the region 610-1040 nm", in Biomedical Topical Meeting on CD-Rom, The Optical Society of America, Washington DC 2004, WF17.

* cited by examiner

APPARATUS AND METHOD FOR ACQUIRING TIME-RESOLVED MEASUREMENTS UTILIZING DIRECT DIGITIZATION OF THE TEMPORAL POINT SPREAD FUNCTION OF THE DETECTED LIGHT

RELATED APPLICATION

This is a nonprovisional application claiming the benefit of provisional application Ser. No. 60/627,147, filed Nov. 15, 2004, incorporated herein by reference.

FIELD OF THE INVENTION

The present invention relates generally to optical imaging systems and particularly to time-resolved optical imaging systems employing pulsed laser light.

BACKGROUND OF THE INVENTION

Many methods exist to nondestructively measure the composition of materials. For materials such as living tissue, x-ray is the oldest method of measurement. Differences in x-ray absorption result from differences in atomic number and differences in density. These differences can be measured by capturing a transmitted x-ray flux on a photographic medium or with an equivalent electronic detector, as in an x-ray computed tomographic scanner. Contrast agents can be introduced, typically with high atomic numbers such as iodine, to enhance features in the tissue. Nuclear tracers and radiopharmaceuticals can be introduced and detected by their emission of typically gamma radiation.

Ultrasound measures acoustic impedance. Sound waves are reflected from boundaries between tissues of differing acoustic impedances, allowing reconstruction of image data from the acoustic signals.

Magnetic resonance imaging detects the presence and chemical composition of certain atoms such as hydrogen and phosphorus in the tissue. Tracer compounds can be introduced, typically with high paramagnetism (e.g. gadolinium), to enhance features in the tissue.

In recent times, the use of light and more specifically laser light to noninvasively reveal the interior structure of the body has been investigated. Optical techniques inject light of one or more wavelengths at one or more locations into tissue and detect light emitted from that tissue at one or more locations.

Continuous wave (CW) optical measurement, employing continuous, unmodulated light, can measure overall light absorption, which is a combination of scattering and attenuation in the tissue. Time-resolved optical measurement, employing very brief light pulses, can distinguish the scattering from attenuation, thus presenting more information regarding the medium being measured. Similarly, frequency domain optical measurements employ light that is modulated at a high frequency, and by measuring the phase and amplitude of the received light, can distinguish the scattering from attenuation.

The scientific paper "Time resolved reflectance and transmittance for the noninvasive measurement of tissue properties", by Patterson, Chance and Wilson, *Applied Optics*, Vol. 28 No. 12, 15 Jun. 1989, develops analytic models from the diffusion equation approximation to the radiative transfer theory. From these models, for a semi-infinite slab of tissue (a good approximation for any relatively large body part), the effective transport scattering coefficient $\mu_s'$ (which is $(1-g)\mu_s$ from this paper) and the absorption coefficient $\mu_a$, can be determined from the shape, duration, and amplitude of the temporal point spread function (TPSF). The approximate double-exponential shape of the TPSF results from the varying number of scattering events each photon encounters while traversing a turbid medium, such as biological tissue. The first photons received presumably have experienced relatively few scattering events, and therefore must have taken the most direct paths from the laser source to the detector probe. The later photons have traveled more circuitous paths through the medium. The early photons may be used to improve the resolution of some optical imaging techniques, especially those derived from x-ray imaging, because the photons' trajectories begin to resemble rays.

The diffusion approximation to the radiative transport equation is given by:

$$\alpha \frac{\partial \Phi}{\partial t} - \nabla^2 \Phi + \beta \Phi = 0$$

A solution to the diffusion equation for an infinite slab is given by:

$$\Phi(t, d) = \frac{1}{t^{3/2}} e^{-\alpha \frac{d^2}{4t}} e^{-(\beta/\alpha)t}$$

$$\text{where: } \alpha = \frac{3(\mu_a + \mu_s')}{nc}, \quad \beta = 3\mu_a(\mu_a + \mu_s'),$$

d is the tissue thickness, $\mu_a$ is the absorption coefficient, $\mu_s'$ is the effective transport scattering coefficient, n is the index of refraction, and c is the speed of light.

FIG. 1 illustrates TPSFs for path lengths of 1.0, 10.0, and 20.0 cm generated using the above solution for the diffusion equation. The optical properties for these simulations were set to $\mu_a$=0.006/mm, $\mu_a'$=0.1/mm and n (index of refraction) =1.33, approximating the bulk tissue optical properties of human breast tissue (see J. Swartling, A. Pifferi, F, Chikoidze, A. Torricelli, P. Taroni, R. Cubeddu, and S. Andersson-Fngels, "Diffuse time-resolved reflectance and transmittance measurements of the female breast using different interfiber distances in the region 610-1040 nm," in Biomedical Topical Meetings on CD-ROM (The Optical Society of America, Washington, D.C., 2004), WF17.) From FIG. 1, the TPSF widths range from less than 2 to more than 8 nanoseconds for path lengths of 1 to 20 cm in human breast tissue.

U.S. Pat. No. 6,339,216 employs a narrow-pulsed mode-locked Ti-Sapphire laser with an analog time-gating circuit to measure both the shape and amplitude of the light signal (the TPSF) emanating from the breast. A single time gate samples each TPSF and is moved across successive TSPFs in order to acquire the entire shape of the pulse, in the fashion of oscilloscope sampling units. The disadvantage of this approach is that if 50 samples are required across the TPSF to adequately characterize it, then 50 TPSFs must be sampled. This approach is fundamentally inefficient.

International Patent Publication WO 2003/009229 A3 extends the concept of a single time gate to multiple gates, in order to collect more information about the TSPF in less total time, therefore shortening the time of an acquisition. This approach is marginally more efficient than that of U.S. Pat. No. 6,339,216, shortening the measurement time by 2× or 3× practically. A dramatic reduction in acquisition times, 10× or 20×, requires the number of fibers all precisely cut to differing lengths.

U.S. Pat. No. 5,386,827 employs a similar analog time-gating circuit for in vivo tissue spectroscopy.

U.S. Pat. No. 5,371,368 employs an optical Kerr cell gate to sample the TPSF, in the fashion of a sampling oscilloscope. The disadvantage of this approach is that if 20 samples are required across the TPSF to adequately characterize it, then 20 TPSFs must be sampled. This approach is fundamentally inefficient.

U.S. Pat. Nos. 5,752,519; 5,555,885; 5,119,815 and 5,148,031 employ time-flight technique to measure the TPSF. This is also referred to as "time-correlated single-photon counting", where the arrival time of each photon is measured with respect to the emission time of the light pulse, usually using a Time-to-Amplitude Converter feeding a MultiChannel Analyzer. Assuming that less than 1 photon arrives per light pulse (a requirement), the histogram of those arrival times will be the shape of the TPSF. This has the disadvantage of being very slow. Thousands of light pulses are required to form a histogram with an acceptable signal-to-noise ratio.

U.S. Pat. No. 4,972,423 employs a streak camera to acquire the TPSF with a very high temporal resolution of 2 picoseconds. The disadvantage of this approach is the extremely high cost and fragility of streak cameras, limiting this approach to laboratory conditions.

OBJECTS AND SUMMARY OF THE INVENTION

It is an object of the present invention to reduce data acquisition time in a time-resolved optical imaging system by directly digitizing the temporal point spread function.

It is another object of the present invention to increase the signal-to-noise ratio of the data obtained from a time-resolved optical imaging system by directly digitizing the temporal point spread function and averaging several TPSFs.

It is still another objective of the present invention to provide processing circuits to allow acquiring data from a scan using a time-resolved optical imaging system to determine the TPSF for a location, and use the TPSF to estimate the transport scattering coefficient $\mu_s'$, and the absorption coefficient, $\mu_a$.

In summary, the present invention provides an apparatus for acquiring time-resolved measurements from a sample from optical scanning, comprising pulsed laser light directed to the sample; a first detector disposed to detect the light after exiting from the sample, the detected light being in the form of a first temporal point spread function (TPSF); a first amplifier to amplify the first TPSF; a first analog-to-digital converted (ADC) to directly digitize the first TPSF; a first buffer connected to the first ADC; a time-pickoff detector to initiate the first ADC to digitize the first TPSF; a clock burst generator initiated by the time-pickoff detector to provide conversion timing to the first ADC; and a computer programmed to fit the digitized first TPSF to a theoretical curve to extract its amplitude, and attenuation and scattering coefficients.

The present invention also provides a method for acquiring time-resolved measurements from a sample from optical scanning, comprising directing a pulse of light onto a surface of the sample; detecting the light that exits from the sample in the form of a temporal point spread function (TPSF); directly digitizing the TPSF; and extracting a transport scattering coefficient and a absorption coefficient from the digitized TPSF.

DETAILED DESCRIPTION OF THE INVENTION

Figure 1:
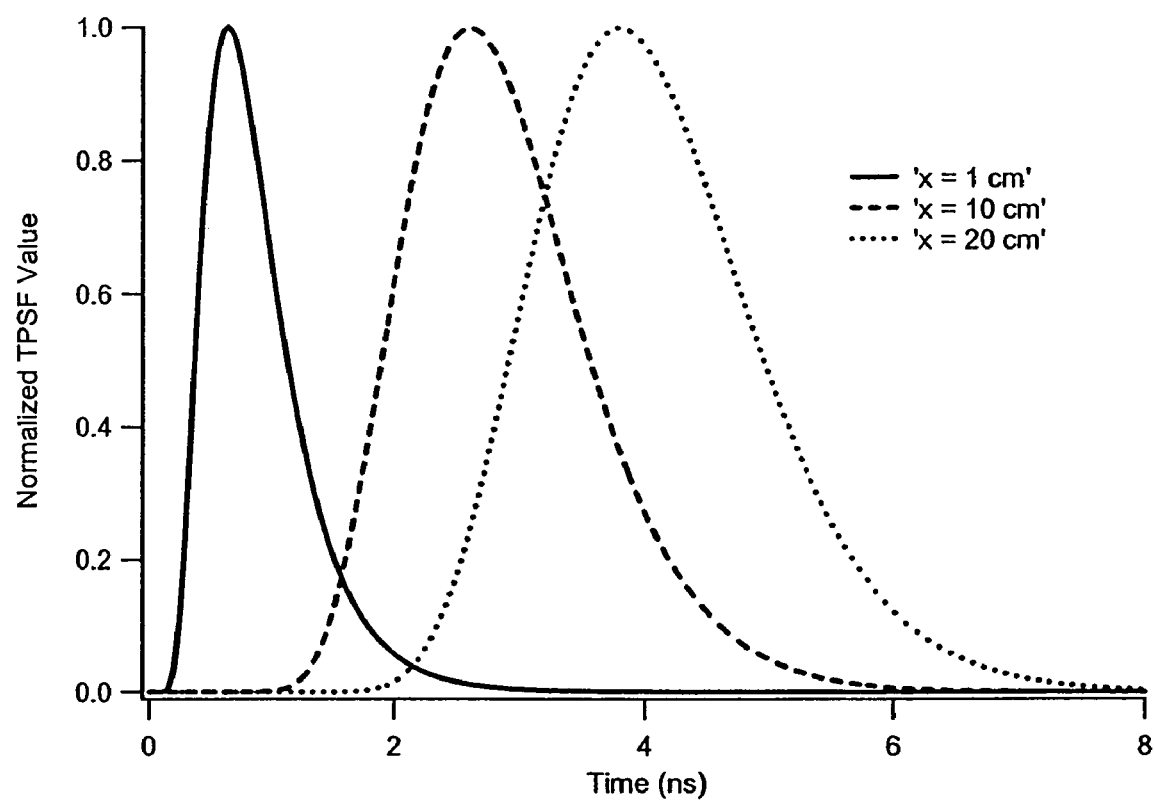
FIG. 1 shows three calculated temporal point spread functions for several tissue thicknesses.
Figure 2:
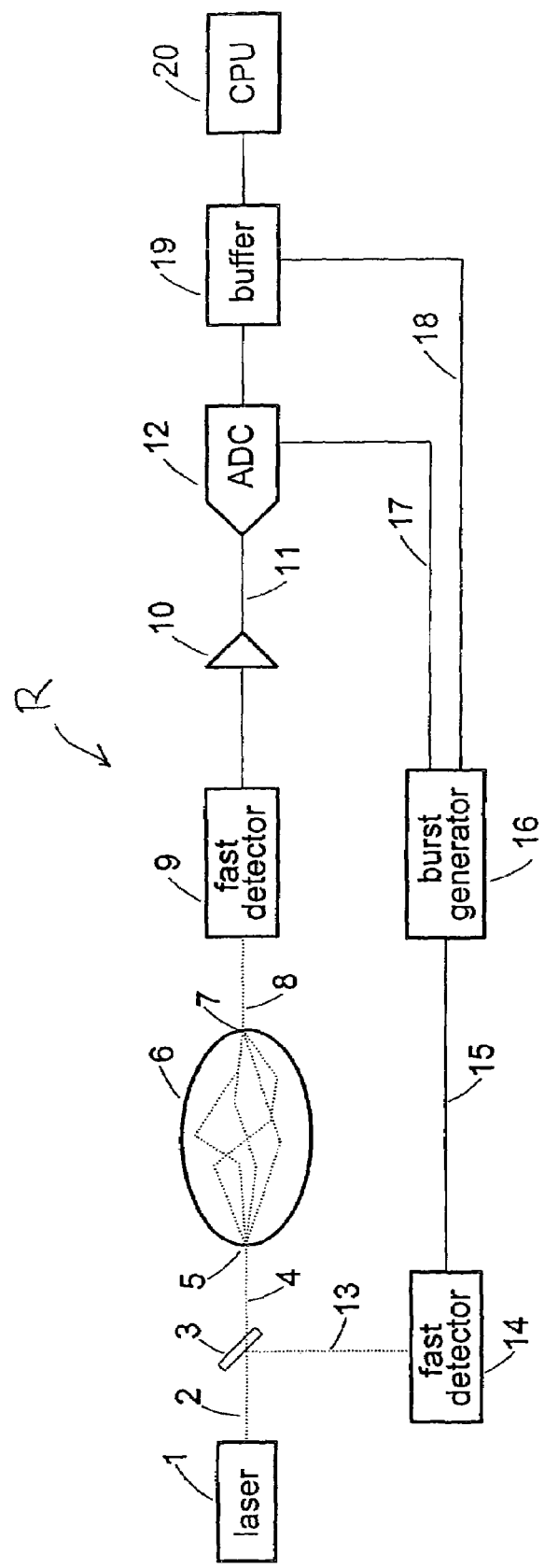
FIG. 2 is a schematic functional block diagram of a time-resolved optical measurement system with a single optical detector in accordance with the present invention.

Referring to FIG. 2, a time-resolved optical measurement system R made in accordance with the present invention is disclosed. A laser 1 produces extremely short, but intense, light pulses 2. Mode-locked Ti-Sapphire lasers have pulse widths in the sub-picosecond range and regeneratively-amplified mode-locked lasers have pulse widths, without compression, in the 10 s-100 s of picoseconds. Fast pulsed diode lasers can also achieve pulse widths well less than 1 nanosecond. The laser output 2 is a periodic light pulse, with pulse width in the femtosecond or picosecond range and repetition rates typically kilohertz to megahertz. A beamsplitter 3 sends most of the light as beam 4 to subject 6, as for example, a female breast. A small portion of the light is reflected as beam 13. Beam 4 enters the subject at location 5 and undergoes multiple scatterings and absorptions. A portion of the incident light ultimately exits the subject, for example at point 7, forming beam 8 and is detected by a fast detector 9. This detector, as well as detector 14, may be a fast photodiode, avalanche photodiode, photomultiplier tube, microchannel plate or any suitably fast optical detector.

Amplifier 10 amplifies the output of the detector 9. The amplifier may be an operational amplifier, a MMIC microwave amplifier, a programmable gain amplifier, a variable gain amplifier, a logarithmic amplifier or some combination of the above. Preferably, the amplifier 10 must have sufficient gain-bandwidth to accommodate the detector output and faithfully reproduce the TPSF. The output of amplifier 10 is signal 11, the temporal point spread function, the TPSF. For cross-sectional breast imaging as an example, the TPSFs will vary in duration between 2 and 20 nanoseconds. The TPSF at this location is the actual TPSF of the subject 6 convolved by the laser output pulse 2. For sufficiently narrow laser pulses, this broadening can be ignored (the laser output can be considered a Dirac delta function).

The amplifier output signal feeds a fast analog to digital converter (ADC) 12. The ADC 12 preferably should have conversion rates in excess of 1 GHz, such as the 1.5 GHz Maxim MAX108 or National Semiconductor ADC081000.

The portion 13 of the laser output pulse is detected by a fast time pickoff detector 14 and converted into a digital trigger pulse 15. The trigger pulse will initiate a clock burst in burst generator 16. The rate of the pulses in the burst is limited by the conversion rate of the ADC 12 and the duration of the burst preferably encompasses the entire TPSF. The clock burst is applied to the ADC 12 as signal 17 and a delayed version of the burst 18 (delayed by the pipeline delay of the ADC) is applied to a buffer 19.

Buffer 19 is a common first-in-first-out (FIFO) buffer. It temporarily stores the fast burst of digitized data from the ADC 12 and will be read out subsequently (between light pulses from the laser), at a much lower rate, into a general purpose computer 20. Depending on the laser pulse rate, the buffer 19 may be in 2 stages: a fast, shallow buffer (10-100 samples deep) followed by a slower, deep buffer with some hardware to copy the first buffer into the second.

The computer 20 is programmed to perform an analysis of the acquired TPSF to extract the transport scattering coefficient, $\mu_s'$ and the absorption coefficient, $\mu_a$. The computer 20 performs a least squares curve fitting of a theoretical model of the TPSF to the acquired data and calculates the best values for $\mu_s'$ and $\mu_a$, and pulse amplitude. Samples from several TPSFs may be averaged to advantageously improve the signal-to-noise ratio of the measurement.

Figure 3:
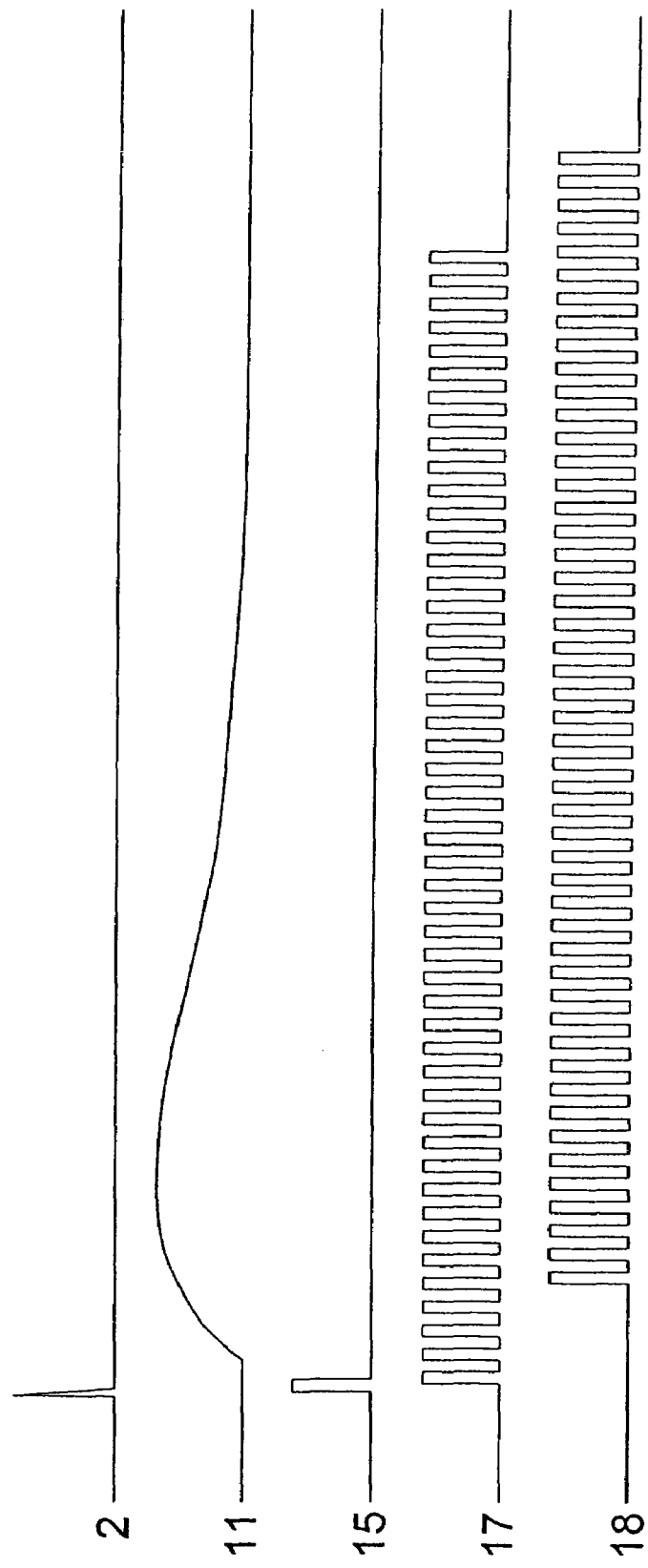
FIG. 3 shows several optical and electrical signals generated within the system of FIG. 2.

Referring to FIG. 3, several signals mentioned in connection with system R are illustrated. Signal 2 is the laser output pulse, which is very narrow, typically well less than 1 nanosecond in width. Signal 11 is the TPSF out of the amplifier 10, showing its relatively fast rise time and longer decay. Signal 15 is the digital trigger pulse from the time pickoff detector 14. The trigger pulse 15 initiates the clock burst, with signal 17 being the conversion clock to the ADC 12 and signal 18 being the input clock to the FIFO buffer 19.

Figure 4:
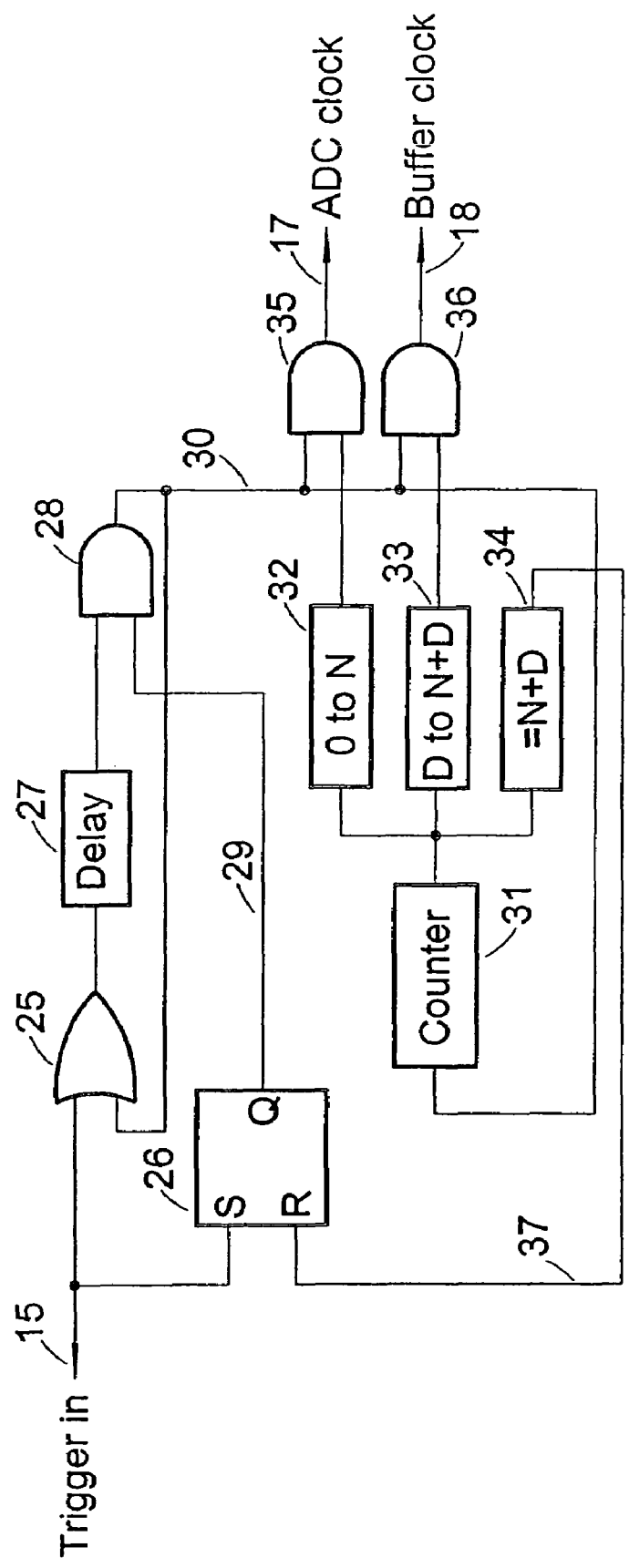
FIG. 4 is a schematic functional block diagram of a clock burst generator used in the present invention.

Referring to FIG. 4, the clock burst generator 16 is disclosed. The circuit shown in FIG. 4 performs the function of generating a clock burst. Trigger input 15 sets the RS flip-flop 26 to the true state, Q high, signal 29. The trigger input also passes through the OR gate 25 and is delayed by the delay 27. The length of this delay will become the period of the ADC clock. The output of the delay passes to AND gate 28, where, since the Q of RS flip-flop 26 is true, will pass the pulse back to the OR gate 25. Thus, this pulse recirculates through the OR gate, delay and AND gate so long as the RS flip-flop is set, thereby forming a pulse train 30, as shown on FIG. 3 as signal 17. The pulse train also clocks a counter 31, typically a binary or Johnson counter. The counter output passes to three comparators. A comparator 32 enables the ADC clock for pulses number 0 through "N", where N is the number of samples to be acquired from each TPSF. An AND gate 35 produces the ADC clock burst 17. A dual-ended comparator 33 enables the FIFO buffer clock for pulses number "D" through "N+D", where D is the ADC's pipeline delay and N is the number of samples to be acquired from each TPSF. An AND gate 36 produces the FIFO buffer clock burst 18. An alternative embodiment would be to delay the ADC clock burst 17 by "N" clock periods and apply that as the FIFO buffer clock 18.

Figure 5:
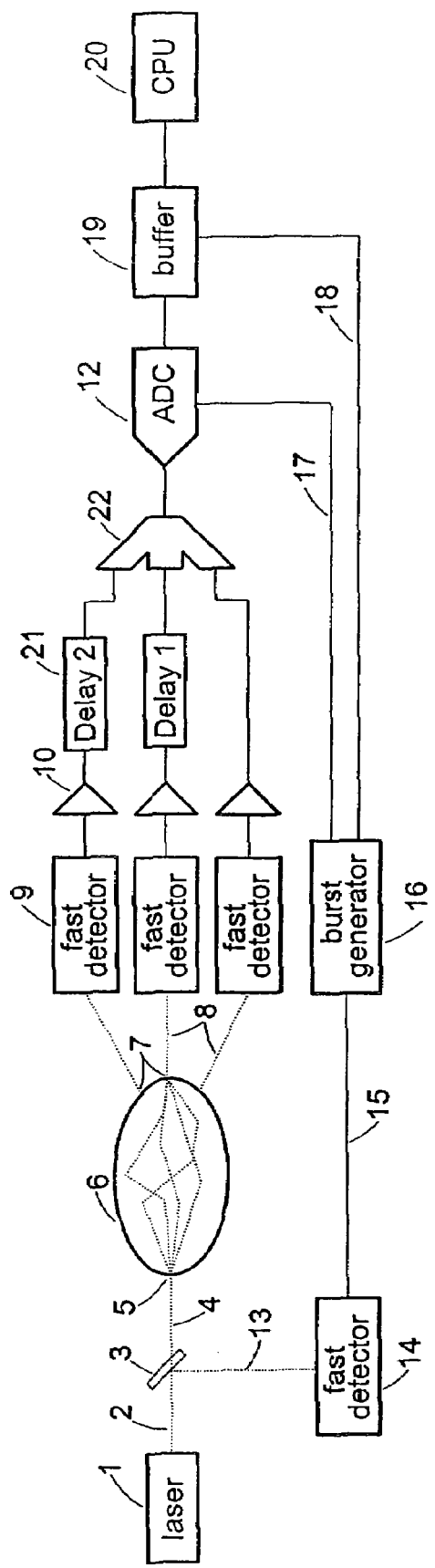
FIG. 5 is a schematic functional block diagram of a time-resolved optical measurement system with multiple detectors.

FIG. 5 expands the optical system R of FIG. 2 to multiple optical detectors sharing one fast ADC 12, as might be employed in an optical computed tomography scanner. Multiple fast detectors 9, each viewing a different area of the surface of object 6, are each connected to their own amplifiers 10 as described above. Each amplifier output is connected to an analog delay 21, with the delays all different in length and time. The delays are connected to one multiplexer 22, which selects each input beginning with the shortest delay (the bottom detector) and proceeding to the longest delay (the top detector). The delays must be longer than the longest anticipated TPSF. If the longest TPSF were anticipated to be 15 nanoseconds, the delay 1 could be 16 nanoseconds, delay 2 could be 32 nanoseconds, etc. The ADC sequentially digitizes all the detectors outputs.

Alternatively, each detector may be configured by optical filters or diffraction gratings to receive a different optical wavelength, as in a multiple wavelength system or a fluorescence excitation system. The time delays between each detector may be alternatively implemented with varied lengths of optical fiber between the object 6 and each fast detector 9.

Figure 6:
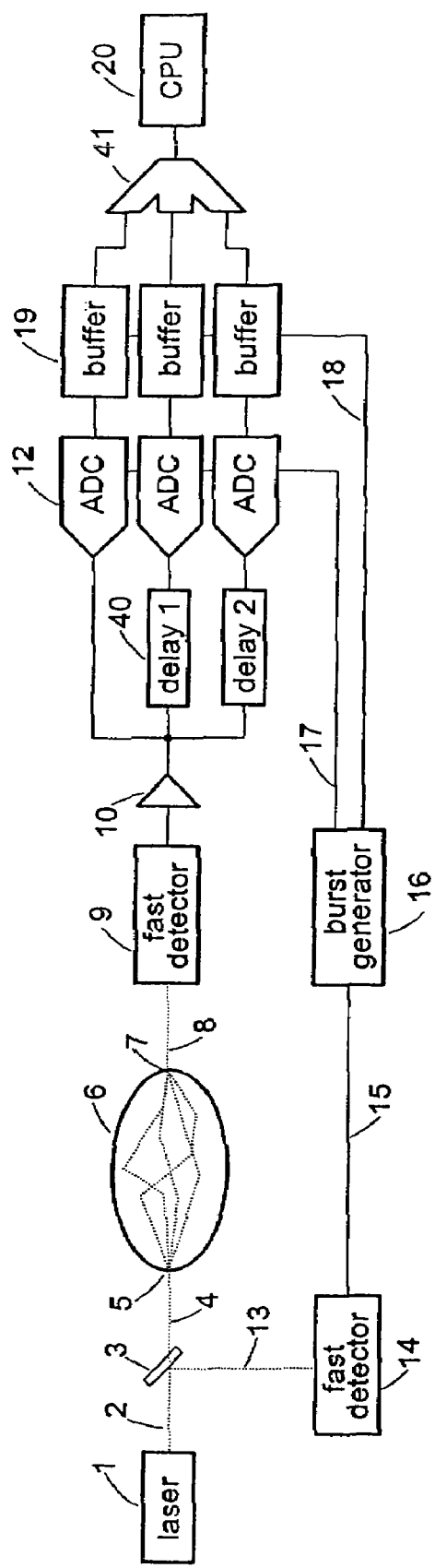
FIG. 6 is a schematic functional block diagram of a time-resolved optical measurement system with multiple analog-to-digital converters (ADCs).

FIG. 6 expands the system R of FIG. 2 to include multiple ADCs 12 with delays 40 on their input signals. The delays would be chosen to be a fraction of the ADC clock 17 burst rate, such that each ADC's sampling point is interleaved with the rest. For example, using three 1.0 GHz sampling-rate ADCs, delay 1 would be 333 picoseconds and delay 2 would be 667 picoseconds. Thus the three ADCs would effect a 3.0 GHz sampling rate. A multiplexer 41 would present the results from the three buffers 19 to the CPU 20 for analysis. Alternatively, the delays could be implemented on the ADC clocks 17 rather than their analog input signals, creating additional clocks, delayed by 333 and 667 picoseconds in the above example.

The above direct digitization technology may be utilized in any number of optical measurement systems. External optical probes used for tissue characterization or blood oxygenation measurements could employ the present invention. The probe could be used in a transmission geometry, with the optical source and detector in opposite sides of the object being measured, or in a reflection mode, with the optical source and detector on the same side of the object being measured. Similarly, internal optical probes, introduced via an endoscope, cannula or needle could employ this technology. This technology could be used in an optical computed tomography scanner, with either fixed source(s) and detector(s) or moving source(s) and detector(s). Optical measurement areas that can employ the present invention include:

Reflectance and transmission spectrophotometry
    In-vitro (optical biopsy)
    Food industry (quality control, product safety)
    Fluorescence lifetime imaging (animal and human, in-vivo and in-vitro)
    Evaluation of pigments and coatings in industry
    Quality assurance-uniformity of pigments in plastics, etc.
Optical Imaging
    Breast cancer detection
    Testicular cancer detection
    Fluorescence lifetime imaging (animal and human, in-vivo and in-vitro)
    Functional imaging (brain and otherwise)
    Finger joints The present invention may also be used in conjunction with fluorescent compounds, in vivo or in vitro. These fluorescent compounds may be organic fluorophores or quantum dots.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. An apparatus for acquiring time-resolved measurements from a sample from optical scanning, comprising:
   a) pulsed laser light directed to a sample;
   b) a first detector disposed to detect the light after exiting from the sample, the detected light being in the form of a first temporal point spread function (TPSF);
   c) a first amplifier to amplify the first TPSF;
   d) a first analog-to-digital converted (ADC) to directly digitize the first TPSF;
   e) a first buffer connected to said first ADC;

f) a time-pickoff detector to initiate said first ADC to digitize the first TPSF;

g) a clock burst generator initiated by said time-pickoff detector to provide conversion timing to said first ADC; and h) a computer programmed to fit the digitized first TPSF to a theoretical curve to extract its amplitude, and attenuation and scattering coefficients.

2. An apparatus as in claim 1, wherein said pulsed laser source is a mode-locked laser light source.

3. An apparatus as in claim 1, wherein said pulsed laser source is a pulsed laser.

4. An apparatus as in claim 1, wherein said pulsed laser source has a pulse width in the femtosecond to picosecond range and repetition rates in the kilohertz to megahertz range.

5. An apparatus as in claim 1, wherein said computer is programmed to average multiple measurements to improve the signal-to-noise ratio of the data.

6. An apparatus as in claim 1, and further comprising:

a) at least a second detector disposed to detect the light after exiting from the sample as a second TPSF;

b) a second amplifier connected to said at least a second detector to amplify the second TPSF;

c) a delay device connected to said at least a second detector to delay the second TPSF by an amount longer than the longest anticipated TPSF;

d) a multiplexer connected to said first amplifier and said delay device;

e) said multiplexer is connected to said first ADC, said multiplexer selecting an input beginning with the shortest delay for processing in sequence by said first ADC.

7. An apparatus as in claim 6, wherein said delay device is an optic fiber.

8. An apparatus as in claim 1, and further comprising:

a) at least one delay device connected to said first amplifier;

b) a second ADC connected to said at least one delay device;

c) a second buffer connected to said second ADC;

d) a multiplexer connected to said first and second buffers; and e) said at least one delay device has a delay configured to be a fraction of a burst rate of said burst generator such that said first and second ADCs have sampling points interleaved in time with each other.

9. An apparatus for acquiring time-resolved measurements from a sample from optical scanning, comprising:

a) pulsed laser light directed to a sample;

b) a first detector disposed to detect the light after exiting from the sample, the detected light being in the form of a first temporal point spread function (TPSF);

c) a first amplifier to amplify the first TPSF;

d) a first analog-to-digital converted (ADC) to directly digitize the first TPSF;

e) a first buffer connected to said first ADC;

f) a time-pickoff detector to initiate said first ADC to digitize the first TPSF;

g) means for generating a clock burst, said means being initiated by said time-pickoff detector to provide conversion timing to said first ADC; and h) a computer programmed to fit the digitized first TPSF to a theoretical curve to extract its amplitude, and attenuation and scattering coefficients.

10. A method for acquiring time-resolved measurements from a sample from optical scanning, comprising:

a) directing a pulse of light onto a surface of the sample;

b) detecting the light that exits from the sample in the form of a temporal point spread function (TPSF);

c) directly digitizing the TPSF; and d) utilizing a time-pickoff detector to trigger said step of directly digitizing the TPSF; and e) extracting a transport scattering coefficient and a absorption coefficient from the digitized TPSF.

11. A method as in claim 10, wherein the pulse of light is a mode-locked laser light source.

12. A method as in claim 10, wherein the pulse of light is a fast pulsed laser.

13. A method as in claim 10, wherein the pulse of light has a pulse width in the femtosecond to picosecond range and repetition rates in the kilohertz to megahertz range.

14. A method as in claim 10, and further comprising the step of generating a clock burst to control said step of directly digitizing the TPSF.

15. A method as in claim 10, and further comprising the step of averaging multiple measurements of the TPSF to improve the signal-to-noise ratio of the data.

16. A method as in claim 10, wherein said extracting step includes the step of fitting the measured TPSF to a theoretical curve to extract the amplitude, attenuation and scattering coefficients.

17. A method as in claim 16, wherein said fitting is implemented with least squares method.

* * * * *